United States Patent
Sherry

(10) Patent No.: US 11,911,262 B2
(45) Date of Patent: Feb. 27, 2024

(54) RATCHET DRIVE DELIVERY FOR SURGICAL IMPLANTS

(71) Applicant: Alcon Inc., Fribourg (CH)

(72) Inventor: R. Mitchell Sherry, Fort Worth, TX (US)

(73) Assignee: Alcon Inc., Fribourg (CH)

( * ) Notice: Subject to any disclaimer, the term of this patent is extended or adjusted under 35 U.S.C. 154(b) by 102 days.

(21) Appl. No.: 17/648,896

(22) Filed: Jan. 25, 2022

(65) Prior Publication Data

US 2022/0241068 A1 Aug. 4, 2022

Related U.S. Application Data

(60) Provisional application No. 63/143,091, filed on Jan. 29, 2021.

(51) Int. Cl.
*A61F 2/16* (2006.01)

(52) U.S. Cl.
CPC ............ *A61F 2/1662* (2013.01); *A61F 2/167* (2013.01); *A61F 2002/1681* (2013.01)

(58) Field of Classification Search
CPC ........ A61F 2/1662; A61F 2/167; A61F 2/966; A61F 2/9661; A61F 2/9662; A61B 2017/2912; A61B 2017/2919; A61B 2017/2923; A61B 17/00; A61B 17/28; A61B 17/2841; A61B 17/29; A61B 17/2909

See application file for complete search history.

(56) References Cited

U.S. PATENT DOCUMENTS

| | | | |
|---|---|---|---|
| 8,579,969 B2 | 11/2013 | Zacharias | |
| 9,408,605 B1 * | 8/2016 | Knodel | ............ A61B 17/07207 |
| 9,480,555 B2 | 11/2016 | Downer et al. | |
| 9,724,191 B2 | 8/2017 | Auld | |
| 10,010,408 B2 | 7/2018 | Auld et al. | |
| 10,172,706 B2 | 1/2019 | Auld et al. | |
| 10,182,939 B2 | 1/2019 | Canelli et al. | |
| 10,226,328 B2 | 3/2019 | Fayyaz et al. | |
| 10,470,875 B2 | 11/2019 | Fayyaz et al. | |
| 2013/0253402 A1 * | 9/2013 | Badawi | ............... A61F 9/00781 604/8 |
| 2016/0120678 A1 | 5/2016 | Green et al. | |
| 2016/0287438 A1 | 10/2016 | Badawi et al. | |
| 2017/0245984 A1 * | 8/2017 | Germann | ........... A61M 5/31586 |
| 2020/0015959 A1 | 1/2020 | Wensrich et al. | |

(Continued)

FOREIGN PATENT DOCUMENTS

| | | |
|---|---|---|
| EP | 1800610 A1 | 6/2007 |
| EP | 3210573 A1 | 8/2017 |

*Primary Examiner* — Sarah W Aleman
(74) *Attorney, Agent, or Firm* — Patterson + Sheridan, LLP

(57) ABSTRACT

An apparatus for delivering an implant to an eye using a ratchet drive. Some embodiments of an apparatus for delivering an implant to an eye may comprise a gear rack configured to be coupled to the implant, a forward gearwheel, an input gearwheel meshed with the forward gearwheel, an idler gearwheel meshed with the input gearwheel, and a reverse gearwheel meshed with the idler gearwheel. An actuation lever may be configured to rotate the input gearwheel. Some embodiments may additionally comprise a pivot arm that may be operable to selectively engage the forward gearwheel and the reverse gearwheel to the gear rack.

14 Claims, 7 Drawing Sheets

(56) References Cited

U.S. PATENT DOCUMENTS

| | | |
|---|---|---|
| 2020/0015960 A1 | 1/2020 | Holderby |
| 2020/0060876 A1 | 2/2020 | Wardle et al. |
| 2020/0093486 A1* | 3/2020 | Somekh ............... A61B 17/068 |
| 2020/0179102 A1 | 6/2020 | Chen et al. |
| 2020/0197159 A1 | 6/2020 | Holderby et al. |
| 2020/0197161 A1 | 6/2020 | Wu |
| 2020/0197167 A1* | 6/2020 | Wensrich ................ A61F 2/167 |
| 2021/0038372 A1 | 2/2021 | Holderby et al. |
| 2021/0361412 A1* | 11/2021 | Zacharias ............... A61F 2/167 |

\* cited by examiner

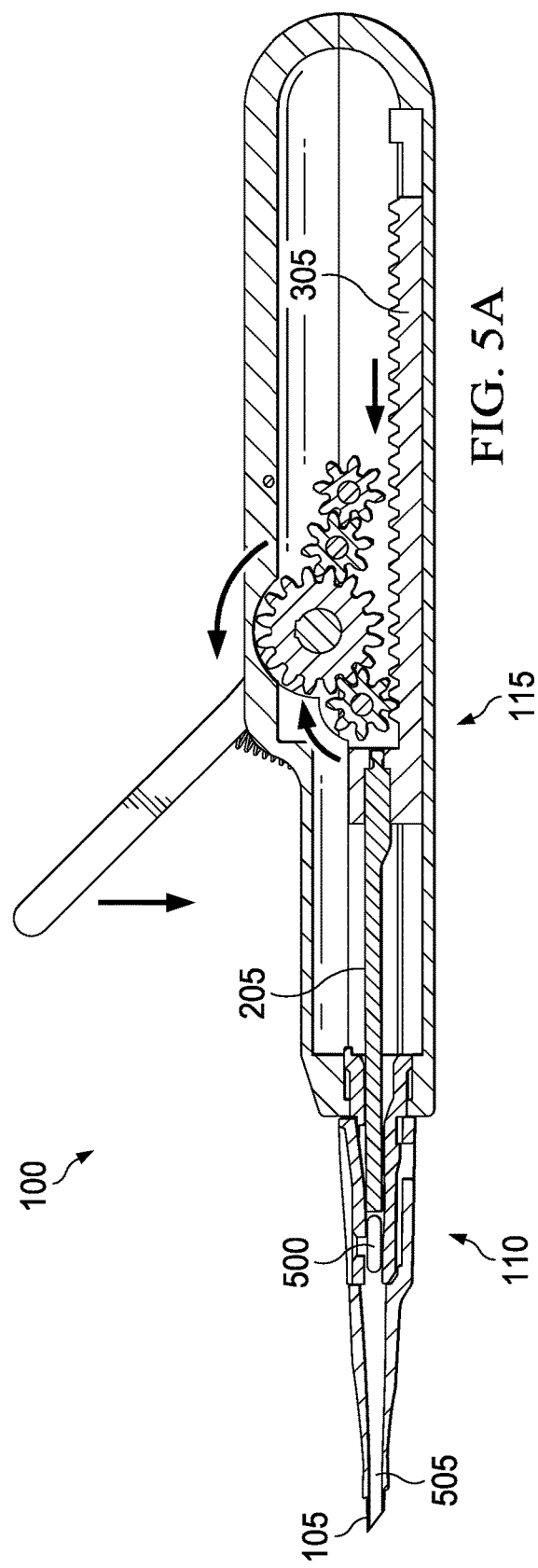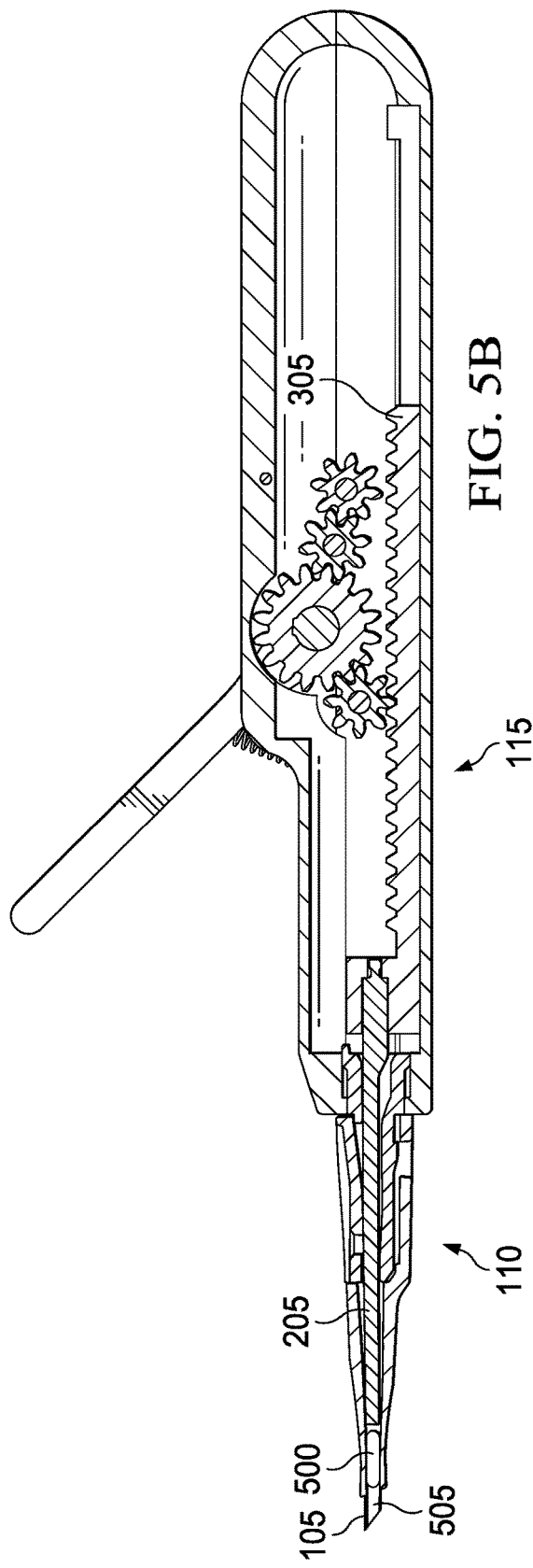

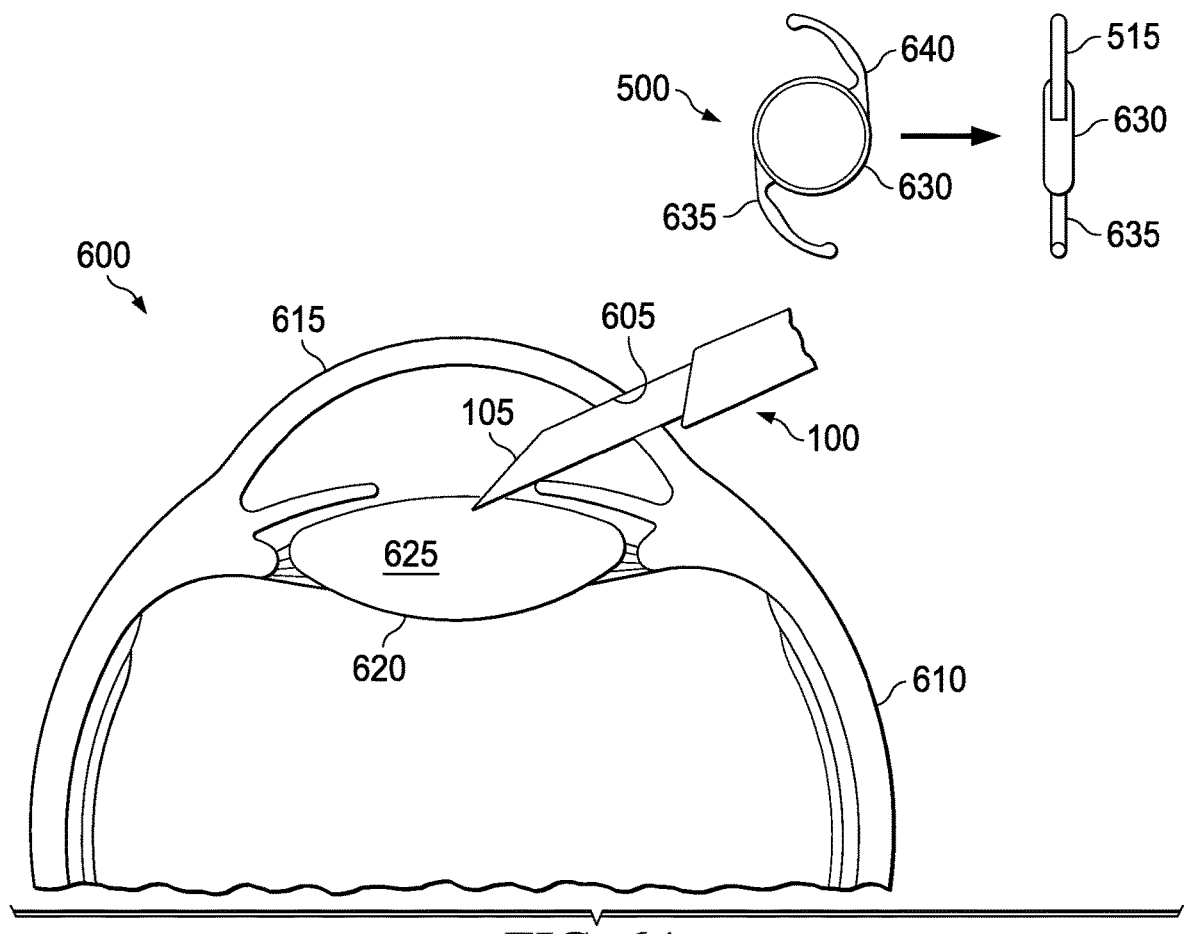
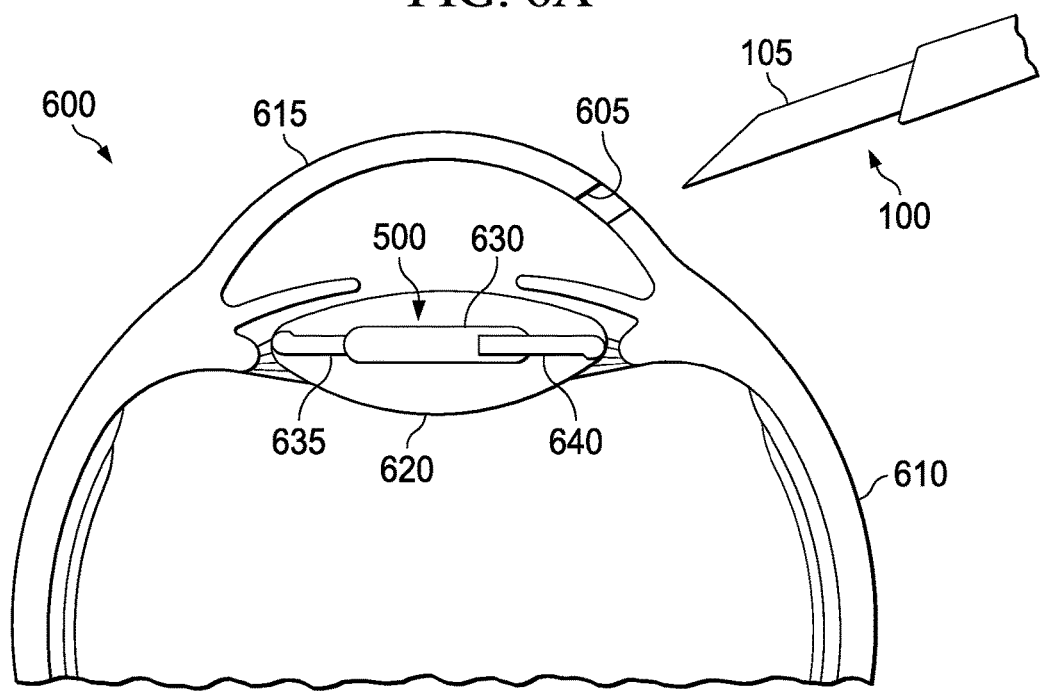
FIG. 6A
FIG. 6B

RATCHET DRIVE DELIVERY FOR SURGICAL IMPLANTS

PRIORITY CLAIM

This application claims the benefit of priority of U.S. Provisional Patent Application Ser. No. 63/143,091 titled "RATCHET DRIVE DELIVERY FOR SURGICAL IMPLANTS," filed on Jan. 29, 2021, whose inventor is R. Mitchell Sherry, which is hereby incorporated by reference in its entirety as though fully and completely set forth herein.

TECHNICAL FIELD

The invention set forth in the appended claims relates generally to eye surgery. More particularly, but without limitation, the claimed subject matter relates to systems, apparatuses, and methods for inserting an implant into an eye.

BACKGROUND

The human eye can suffer a number of maladies causing mild deterioration to complete loss of vision. While contact lenses and eyeglasses can compensate for some ailments, ophthalmic surgery may be required for others. In some instances, implants may be beneficial or desirable. For example, an intraocular lens may replace a clouded natural lens within an eye to improve vision.

While the benefits of intraocular lenses and other implants are known, improvements to delivery systems, components, and processes continue to improve outcomes and benefit patients.

BRIEF SUMMARY

New and useful systems, apparatuses, and methods for eye surgery are set forth in the appended claims. Illustrative embodiments are also provided to enable a person skilled in the art to make and use the claimed subject matter.

Some embodiments may provide a reusable or disposable, manually operated, one-handed delivery device that can drive a plunger or other type of push rod smoothly and reliably. For example, an example apparatus may comprise a geared drive mechanism, which can be driven by a lever-operated ratcheting arrangement. Some embodiments may incorporate, among other things, drive gears and driven gears, idler gears, an actuation lever, a drive pawl and anti-reverse pawl, a spring to return the lever to a starting position, and a forward/reverse switch. The lever may be manually powered by the index finger of either hand in some embodiments.

In more particular examples, a delivery apparatus may comprise a collection of gears mounted to a pivot plate, a lever, and a ratchet to produce linear motion of a gear rack. The linear motion may drive a plunger or rod to advance an implant. In some embodiments, the apparatus can interface with the implant to prepare an implant for delivery. For example, a plunger may fold an implant before advancing the implant into an eye. The gear arrangement may include a drive gear that meshes with a forward gear and an idler gear. The idler gear may, in turn, mesh with a reverse gear. A lever may interact with a ratchet mechanism to rotate the drive gear and ensure positive drive in only one direction during operation. A drive pawl and optional anti-reverse pawl can control the ratchet. A spring can be employed to return the lever to a starting position if released. In some embodiments, a manually operated switch can determine the direction of travel (i.e., forward or reverse) by rotating the pivot plate so the intended gear is engaged with the gear rack.

More generally, some embodiments of an apparatus for delivering an implant to an eye may comprise a gear rack configured to be coupled to the implant, a forward gearwheel, an input gearwheel meshed with the forward gearwheel, an idler gearwheel meshed with the input gearwheel, and a reverse gearwheel meshed with the idler gearwheel. An actuation lever may be configured to rotate the input gearwheel, thereby causing other gears to move the gear rack. Some embodiments may additionally comprise a pivot arm, which may be operable to selectively engage the forward gearwheel and the reverse gearwheel to the gear rack.

In more particular embodiments, the apparatus may comprise a ratchet wheel coupled to the actuation lever and the input gearwheel. The ratchet wheel may be configured to allow the actuation lever to rotate the input gearwheel in only one direction. An input shaft may couple the actuation lever to the input gearwheel in some embodiments, and the pivot arm may be operable to pivot about the input shaft. For example, the pivot arm may be operable to rotate between a first position and a second position. The first position may engage the forward gearwheel to the gear rack, and the second position may engage the reverse gearwheel to the gear rack. Some embodiments may comprise a spring configured to return the pivot arm to the first position.

More particular embodiments may additionally comprise a nozzle having a delivery lumen, an implant bay coupled to the nozzle, and a push rod configured to couple the gear rack to the implant in the implant bay. The push rod may also be configured to advance the implant into the delivery lumen.

Features, elements, and aspects described in the context of some embodiments may also be omitted, combined, or replaced by alternative features. Other features, objectives, advantages, and a preferred mode of making and using the claimed subject matter are described in greater detail below with reference to the accompanying drawings of illustrative embodiments.

BRIEF DESCRIPTION OF THE DRAWINGS

The accompanying drawings illustrate some objectives, advantages, and a preferred mode of making and using some embodiments of the claimed subject matter. Like reference numbers represent like parts in the examples.

FIG. 5A and FIG. 5B are schematic diagrams illustrating an example method of ejecting an implant from the apparatus of FIG. 1.

FIG. 6A and FIG. 6B are schematic diagrams illustrating an example application of the apparatus of FIG. 1 to insert an implant into an eye.

DESCRIPTION OF EXAMPLE EMBODIMENTS

The following description of example embodiments provides information that enables a person skilled in the art to make and use the subject matter set forth in the appended claims, but it may omit certain details already well known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive an implant. However, as should be recognized by those skilled in the art, this frame of reference is merely a descriptive expedient rather than a strict prescription.

Figure 1:
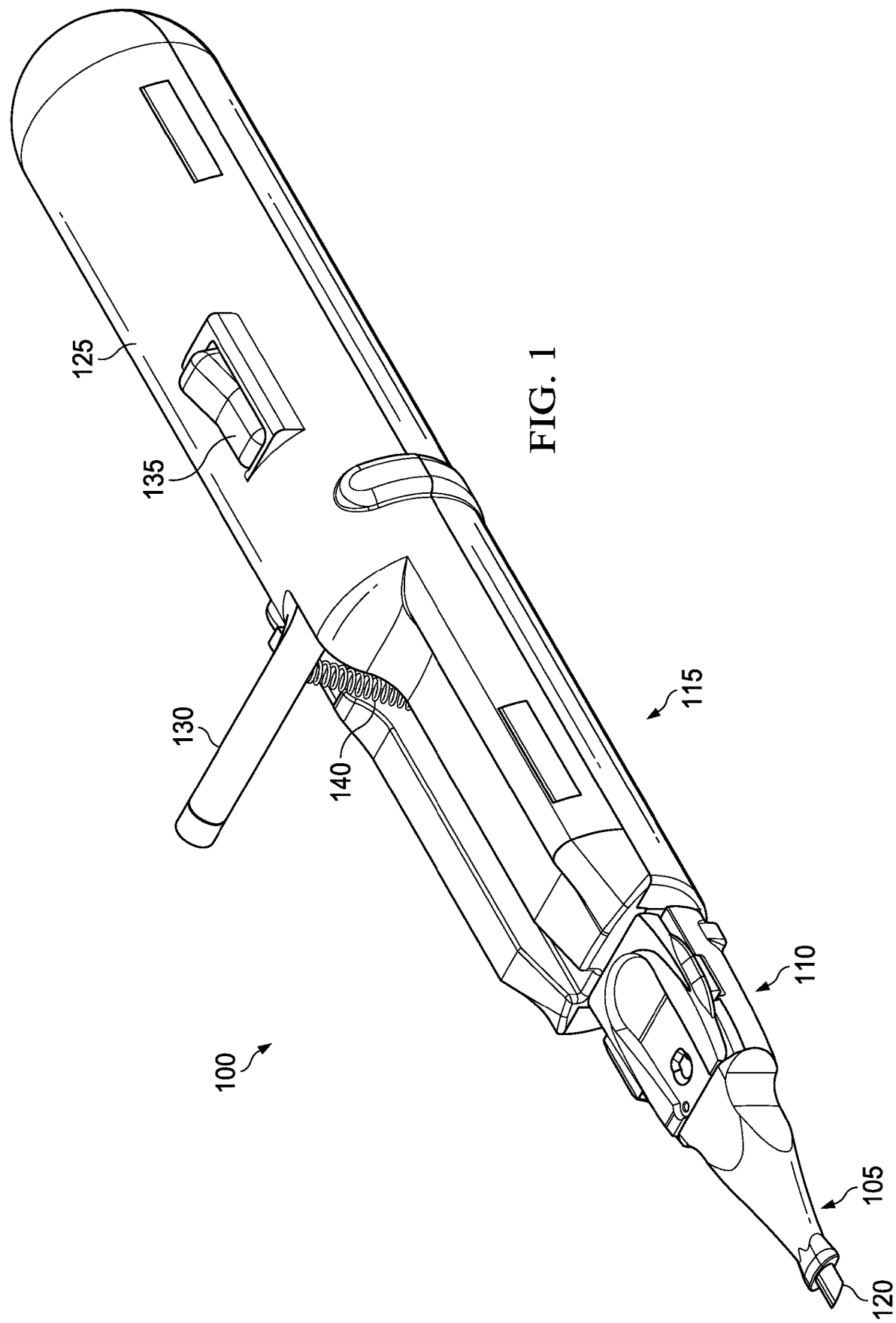
FIG. 1 is an isometric view of an example apparatus for delivering an implant into an eye.

FIG. 1 is an isometric view of an example of an apparatus 100 that can deliver an implant into an eye. In some embodiments, the apparatus 100 may comprise two or more modules, which can be configured to be coupled and decoupled as appropriate for storage, assembly, use, and disposal. As illustrated in FIG. 1, some embodiments of the apparatus 100 may include a nozzle 105, an implant bay 110 coupled to the nozzle 105, and an actuator 115 coupled to the implant bay 110.

The nozzle 105 generally comprises a tip 120 adapted for insertion through an incision into an eye. The size of the tip 120 may be adapted to surgical requirements and techniques as needed. For example, small incisions are generally preferable to reduce or minimize healing times. Incisions of less than 3 millimeters may be preferable in some instances, and the tip 120 of the nozzle 105 may have a width of less than 3 millimeters in some embodiments.

The implant bay 110 generally represents a wide variety of apparatuses that are suitable for storing an implant prior to delivery into an eye. In some embodiments, the implant bay 110 may additionally or alternatively be configured to prepare an implant for delivery. For example, some embodiments of the implant bay 110 may be configured to be actuated by a surgeon or other operator to prepare an implant for delivery by subsequent action of the actuator 115. In some instances, the implant bay 110 may be configured to actively deform, elongate, extend, or otherwise manipulate features of the implant before the implant is advanced into the nozzle 105. For example, the implant bay 110 may be configured to extend or splay one or more features, such as haptics, of an intraocular lens.

The actuator 115 is generally configured to advance an implant from the implant bay 110 into the nozzle 105, and thereafter from the nozzle 105 through an incision and into an eye. In the example of FIG. 1, the actuator 115 additionally comprises a housing 125, an actuation lever 130, and a rocker switch 135. The actuation lever 130 and the rocker switch 135 can be configured to allow an operator to manually operate the actuator 115. In some embodiments, the actuator 115 may additionally comprise a return spring 140, which may be coupled to the actuation lever 130 and the housing 125.

In general, components of the apparatus 100 may be coupled directly or indirectly. For example, the nozzle 105 may be directly coupled to the implant bay 110 and may be indirectly coupled to the actuator 115 through the implant bay 110. Coupling may include fluid, mechanical, thermal, electrical, or chemical coupling (such as a chemical bond), or some combination of coupling in some contexts. For example, implant bay 110 may be mechanically coupled to the actuator 115 and may be mechanically and fluidly coupled to the nozzle 105. In some embodiments, components may also be coupled by virtue of physical proximity, being integral to a single structure, or being formed from the same piece of material.

Figure 2:
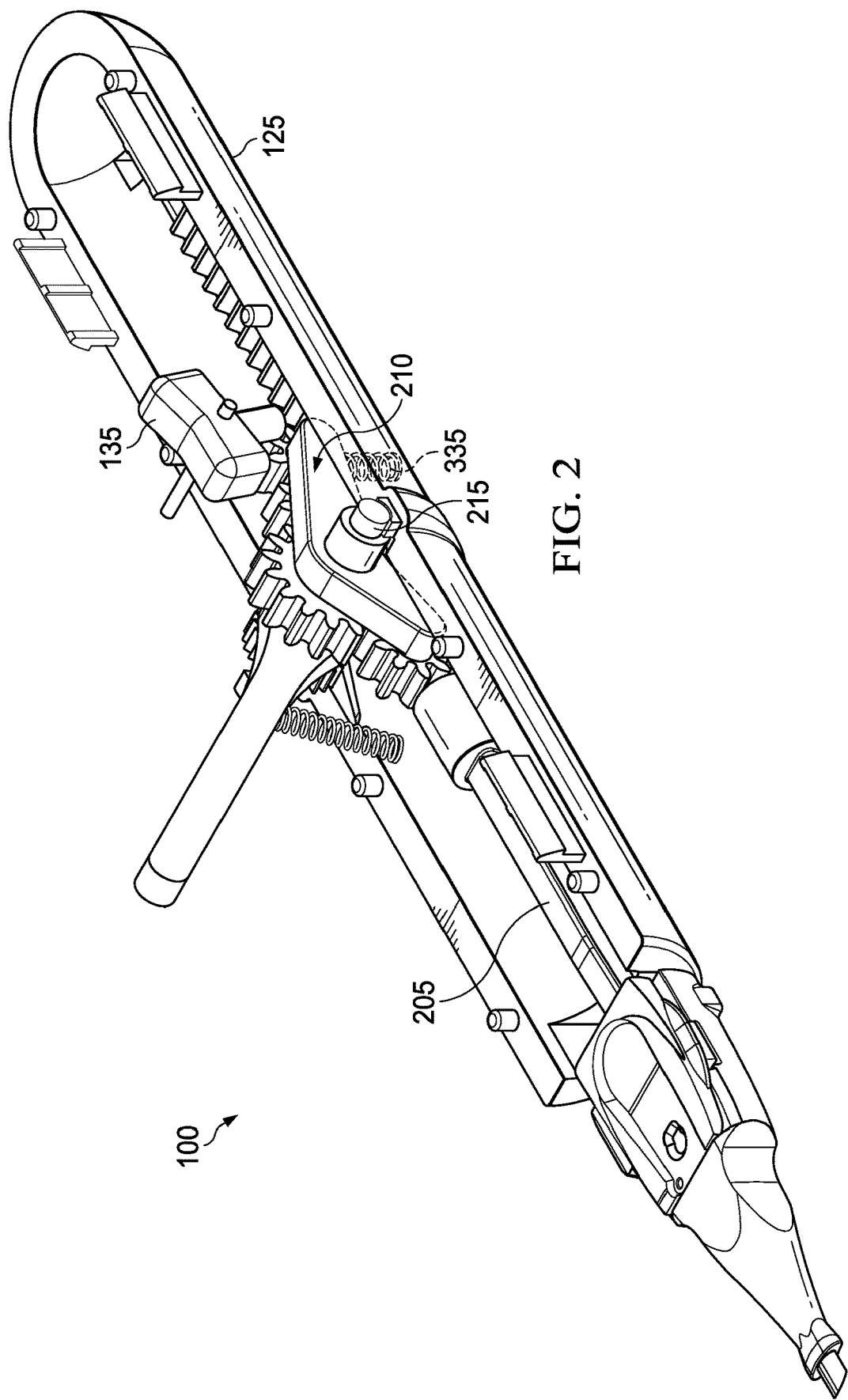
FIG. 2 is an isometric view of a portion of the example apparatus of FIG. 1, illustrating additional details of a drive assembly that may be associated with some embodiments.

FIG. 2 is an isometric view of the apparatus 100 of FIG. 1 with a portion of the housing 125 removed to illustrate additional details that may be associated with some embodiments. As illustrated in the example of FIG. 2, in some embodiments the housing 125 may enclose a push rod 205 and a drive assembly 210. The push rod 205 is generally comprised of a substantially rigid material, such as a medical grade polymer material. The housing 125 may at least partially support the drive assembly 210. For example, in FIG. 2 the drive assembly 210 comprises an input shaft 215, which may be coupled to the housing 125 to support the drive assembly 210.

Figure 3:
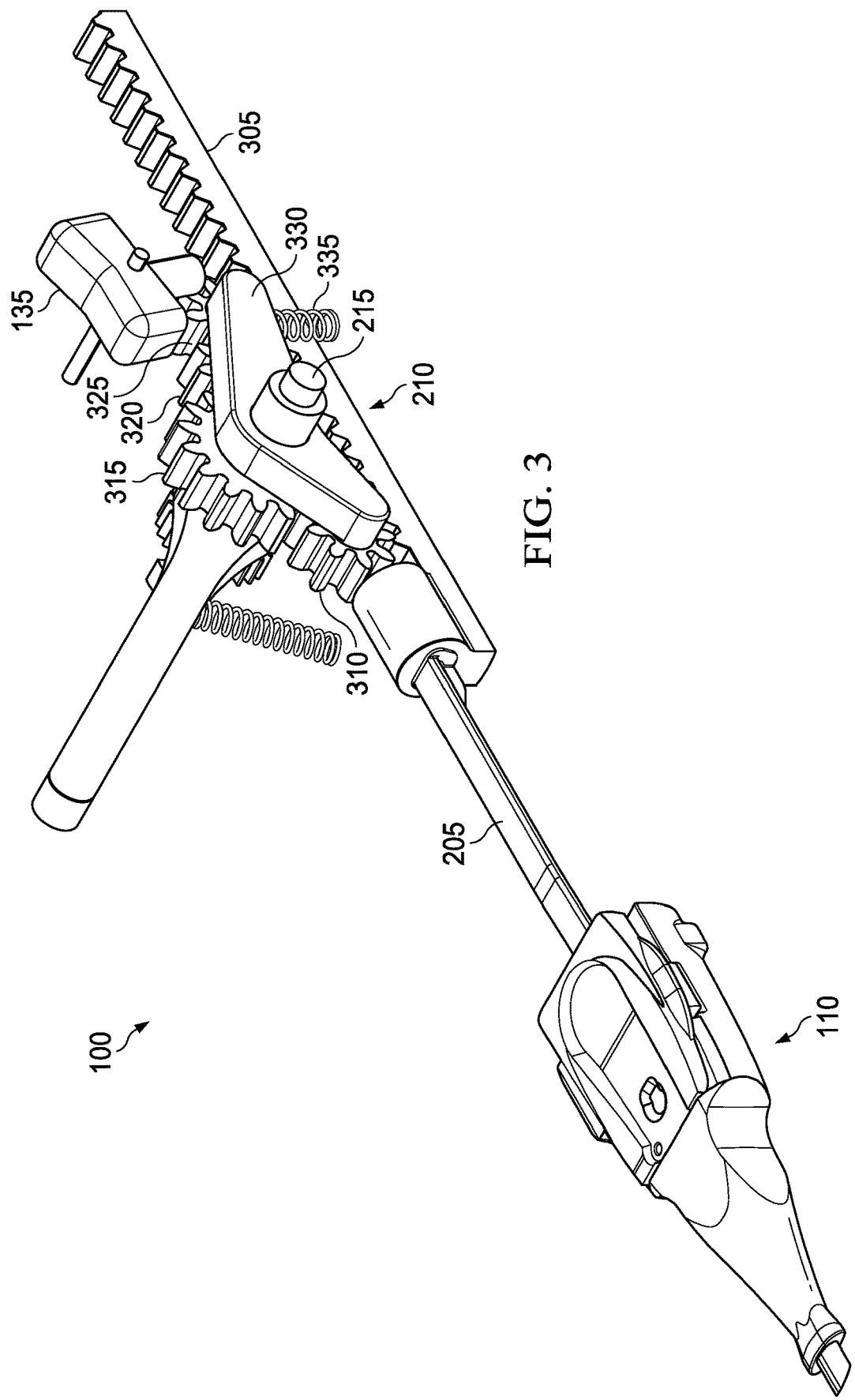
FIG. 3 is another isometric view of a portion of the example apparatus of FIG. 1, illustrating additional details that may be associated with some embodiments of a drive assembly.

FIG. 3 is an isometric view of the apparatus 100 of FIG. 2 with the remainder of the housing 125 removed to illustrate additional details that may be associated with some embodiments of the drive assembly 210. As illustrated in the example of FIG. 3, some embodiments may comprise a gear rack 305, a forward gearwheel 310, an input gearwheel 315, an idler gearwheel 320, a reverse gearwheel 325, and a pivot arm 330.

The pivot arm 330 may be operable to pivot or otherwise rotate about the input shaft 215. In some embodiments, the pivot arm 330 may be rotatably mounted on the input shaft 215. For example, the pivot arm 330 may be coupled to the rocker switch 135, which can be activated by an operator to rotate the pivot arm 330. A return spring 335 may be configured to return the pivot arm 330 if the rocker switch 135 is deactivated. For example, one end of the return spring 335 may be supported by the housing 125 (not shown) and the other may be coupled to the pivot arm 330 as illustrated in FIG. 3, which can provide a restoring force to rotate the pivot arm 330 to a resting position.

Figure 4A:
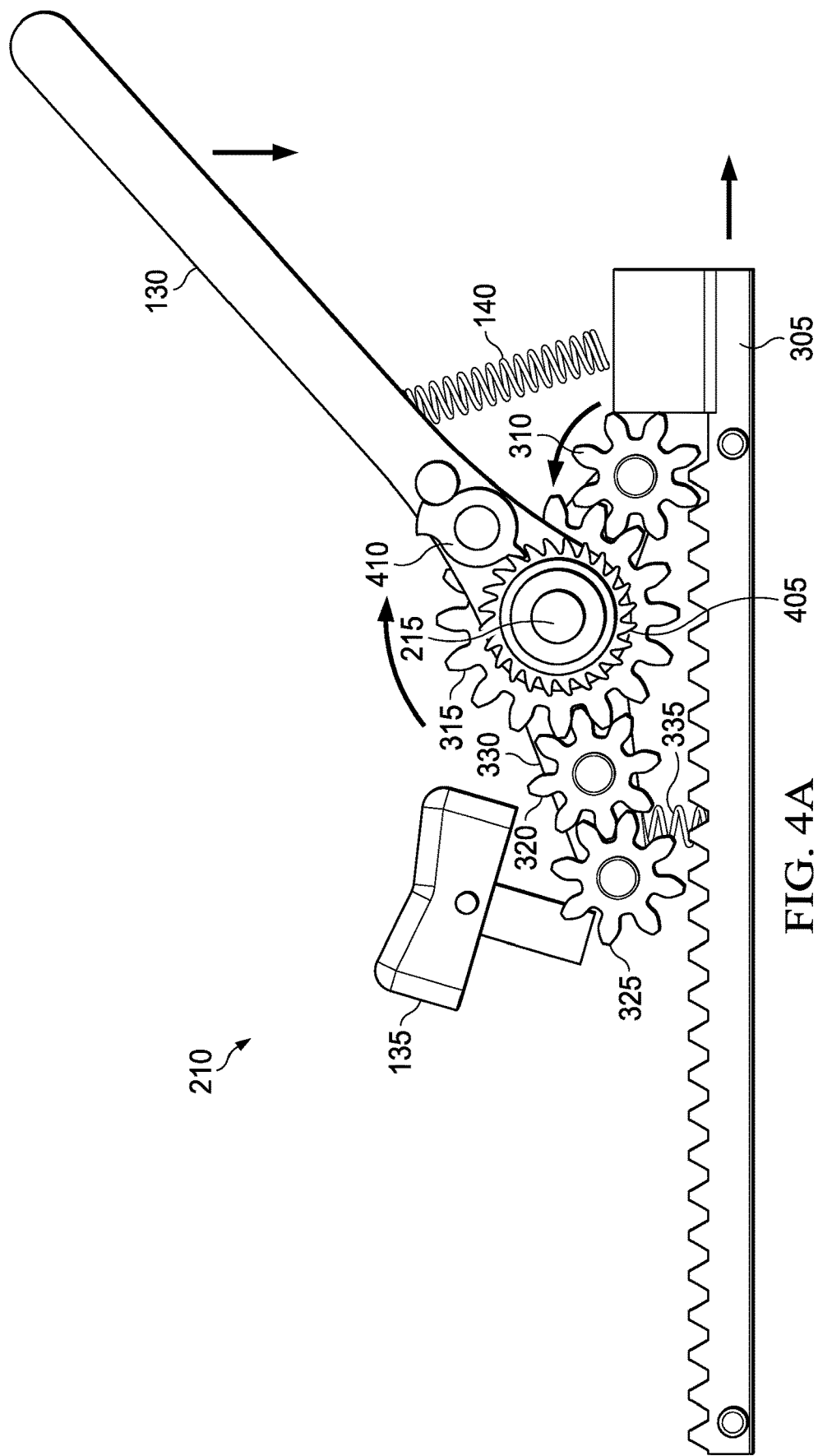
FIG. 4A and FIG. 4B are rear views of the drive assembly of FIG. 3 in different positions.
Figure 4B:
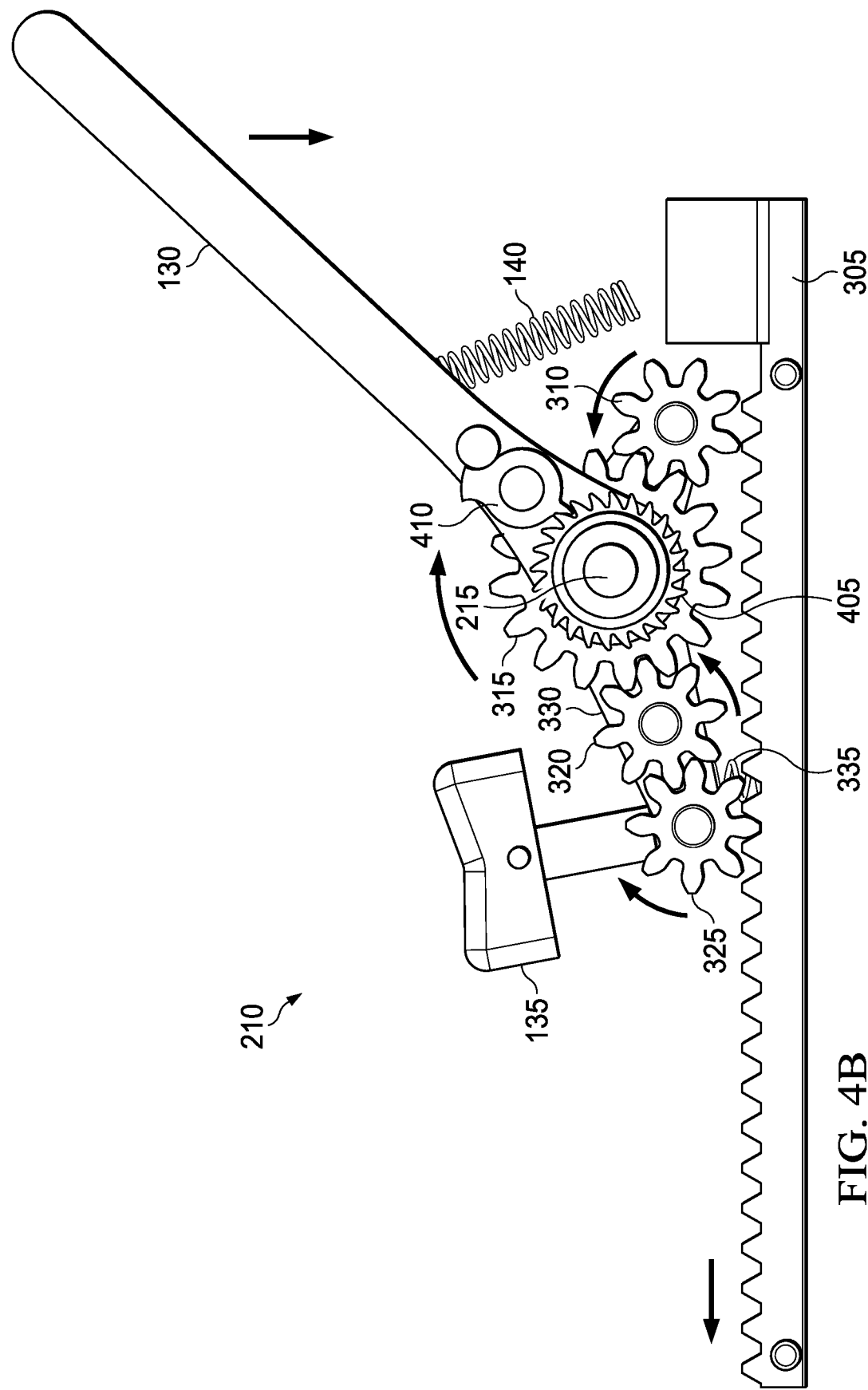

FIG. 4A and FIG. 4B are rear views of the drive assembly 210 of FIG. 3 in different positions. As illustrated in the example of FIG. 4A and FIG. 4B, the forward gearwheel 310, the idler gearwheel 320, and the reverse gearwheel 325 may be rotatably mounted on the pivot arm 330. The pivot arm 330 may be operable to selectively engage and disengage the forward gearwheel 310 and the reverse gearwheel 325 to the gear rack 305. For example, the pivot arm 330 may be rotatably mounted on the input shaft 215, and the rocker switch 135 may be activated to rotate the pivot arm 330 about the input shaft 215 between a first position illustrated in FIG. 4A and a second position illustrated in FIG. 4B.

The input shaft 215 may couple the actuation lever 130 to the input gearwheel 315. For example, as illustrated in FIG. 4A and FIG. 4B, some embodiments of the drive assembly 210 may comprise a ratchet wheel 405 that indirectly couples the actuation lever 130 and the input gearwheel 315. In some embodiments, a pawl 410 may indirectly couple the ratchet wheel 405 to the actuation lever 130. The ratchet wheel 405 may be configured to allow the actuation lever 130 to rotate the input gearwheel 315 in only one direction. For example, in FIG. 4A and FIG. 4B, the input gearwheel 315 and the ratchet wheel 405 may be rigidly coupled or otherwise rotationally fixed relative to the input shaft 215 so that the input shaft 215, the input gearwheel 315, and the ratchet wheel 405 rotate simultaneously. Movement of the actuation lever 130 in a first direction (downward in the example of FIG. 4A and FIG. 4B) can cause the pawl 410 to engage asymmetrical teeth on the ratchet wheel 405, which can cause rotation of the ratchet wheel 405 in a first direction (clockwise in the example of FIG. 4A and FIG. 4B). In the example of FIG. 4A and FIG. 4B, rotation of the ratchet wheel 405 in the first direction also can cause rotation of the input shaft 215 and the input gearwheel 315 in the first direction. Reverse movement of the actuation lever 130 can cause the pawl 410 to slide over the asymmetrical teeth on the ratchet wheel 405, substantially reducing or preventing reverse movement of the ratchet wheel 405, the input shaft 215, and the input gearwheel 315.

In FIG. 4A, the pivot arm 330 is illustrated in a first position. In the first position of FIG. 4A, the forward gearwheel 310 may be meshed or otherwise engaged with the gear rack 305, and the input gearwheel 315 may be meshed with the forward gearwheel 310. The idler gearwheel 320 may be meshed with the input gearwheel 315, and the reverse gearwheel 325 may be meshed with the idler gearwheel 320. The reverse gearwheel 325 is disengaged from the gear rack 305 in the first position of the pivot arm 330 illustrated in the example of FIG. 4A.

With the pivot arm 330 in the first position of FIG. 4A, the forward gearwheel 310 is engaged to the gear rack 305 and the reverse gearwheel 325 is disengaged. In this first position, movement of the actuation lever 130 toward the forward gearwheel 310 (i.e., forward or downward in the orientation of FIG. 4A) causes the pawl 410 to engage the ratchet wheel 405 and rotate the ratchet wheel 405 in a first direction (i.e., clockwise in the orientation of FIG. 4A), thereby also rotating the input shaft 215 and the input gearwheel 315 in the same direction. Rotation of the input gearwheel 315 in the first direction simultaneously causes the forward gearwheel 310 to rotate in the opposite direction (i.e., counterclockwise in the orientation of FIG. 4A). Rotation of the forward gearwheel 310 in this direction, while engaged to the gear rack 305 as in the example of FIG. 4A, causes the gear rack 305 to advance in a first direction (i.e., rightward in the orientation of FIG. 4A). The movement of the actuation lever 130 can be reversed to reset the actuation lever 130 and allow for further advancement of the gear rack 305 as appropriate. In the example of FIG. 4A, the pawl 410 can slide over the teeth of the ratchet wheel 405 as the actuation lever 130 moves in the reverse direction without causing rotation of the input shaft 215. In some embodiments, the return spring 140 can reverse and reset the actuation lever 130.

With the pivot arm 330 in the second position of FIG. 4B, the forward gearwheel 310 is disengaged from the gear rack 305 and the reverse gearwheel 325 is engaged to the gear rack 305. In this second position, movement of the actuation lever 130 toward the forward gearwheel 310 can cause the pawl 410 to engage the ratchet wheel 405 and rotate the ratchet wheel 405 in the first direction, thereby also rotating the input shaft 215 and the input gearwheel 315 in the same direction. Rotation of the input gearwheel 315 in the first direction simultaneously can cause the idler gearwheel 320 to rotate in the opposite direction, which in turn can cause the reverse gearwheel 325 to rotate in the same direction as the input gearwheel 315. Rotation of the reverse gearwheel 325 in this direction, while engaged to the gear rack 305 as in the example of FIG. 4B, can cause the gear rack 305 to retract in a second direction, thereby reversing the direction of movement in the example of FIG. 4A.

The return spring 335 may provide a restoring force to the pivot arm 330 to return the forward gearwheel 310 to the gear rack 305 and disengage the reverse gearwheel 325 if the rocker switch 135 is deactivated.

FIGS. 5A-5B are schematic diagrams illustrating an example method of ejecting an implant 500 from the apparatus 100. Initially, various components of the system may be assembled if needed or appropriate. In the example of FIGS. 5A-5B, the nozzle 105, the implant bay 110, and the actuator 115 are fixed together to form a unitary structure. In other embodiments, the apparatus 100 may comprise two or more modules, which can be configured to be coupled and decoupled as appropriate for storage, assembly, use, and disposal.

As illustrated in the example of FIG. 5A, the implant 500 may be initially stored in the implant bay 110. The gear rack 305 may be configured to be coupled to the implant 500 in the implant bay 110. For example, the gear rack 305 may be indirectly coupled to the implant 500 through the push rod 205. In other examples, the gear rack 305 may be configured to be directly coupled to the implant 500. As illustrated in the example of FIG. 5A, at least a portion of the push rod 205 may extend into the implant bay 110. In some embodiments, the push rod 205 may be configured to engage the implant 500 in the implant bay 110. In some embodiments, the implant 500 may comprise an intraocular lens having a shape similar to that of a natural lens of an eye, and it may be made from numerous materials. Examples of suitable materials may include silicone, acrylic, and combinations of such suitable materials. In some instances, the implant 500 may comprise an intraocular lens that is fluid-filled, such as a fluid-filled accommodating intraocular lens. The implant 500 may also comprise an intraocular lens that includes one or more features, such as haptics, for positioning the intraocular lens within an eye.

In some embodiments, the implant bay 110 may additionally or alternatively be configured to prepare the implant 500 for delivery. For example, some embodiments of the implant bay 110 may be configured to be actuated by a surgeon or other operator to prepare the implant 500 for delivery by subsequent action of the actuator 115. In some instances, the implant bay 110 may be configured to actively deform, elongate, extend, or otherwise manipulate features of the implant 500 before the implant 500 is advanced into the nozzle 105. For example, some embodiments of the implant bay 110 may be configured to orient or fold an implant. Some embodiments of the implant 500 may comprise one or more haptics, which can be oriented for delivery.

The push rod 205 is generally configured to advance the implant 500 from the implant bay 110 into a delivery lumen 505 of the nozzle 105. For example, if the forward gearwheel 310 is engaged to the gear rack 305, the gear rack 305 can be advanced substantially as described with reference to FIG. 4A, which can advance the push rod 205 from a first position illustrated in FIG. 5A to a second position illustrated in FIG. 5B. Advancement of the push rod 205, in turn, can advance the implant 500 from the implant bay 110 to the delivery lumen 505 as illustrated.

FIGS. 6A-6B are schematic diagrams further illustrating an example use of the apparatus 100 to deliver the implant 500 to an eye 600. As illustrated, an incision 605 may be made in the eye 600 by a surgeon, for example. In some instances, the incision 605 may be made through the sclera 610 of the eye 600. In other instances, an incision may be formed in the cornea 615 of the eye 600. The incision 605 may be sized to permit insertion of a portion of the nozzle 105 in order to deliver the implant 500 into the capsular bag 620. For example, in some instances, the size of the incision 605 may have a length less than about 3000 microns (3 millimeters). In other instances, the incision 605 may have a length of from about 1000 microns to about 1500 microns, from about 1500 microns to about 2000 microns, from about 2000 microns to about 2500 microns, or from about 2500 microns to about 3000 microns.

After the incision 605 is made, the nozzle 105 can be inserted through the incision 605 into an interior portion 625 of the eye 600. The apparatus 100 can then eject the implant 500 through the nozzle 105 into the capsular bag 620 of the eye 600, substantially as described with reference to FIG. 5A and FIG. 5B. In the example of FIG. 6A and FIG. 6B, the implant 500 is illustrative of an intraocular lens having an optic body 630, a leading haptic 635, and a trailing haptic 640. In some applications, the implant 500 may be delivered in a straightened configuration, with one or both of the leading haptic 635 and the trailing haptic 640 in a splayed configuration, and can revert to an initial, resting state with the leading haptic 635 and the trailing haptic 640 being at least partially curved around the optic body 630, within the capsular bag 620, as shown in FIG. 6B. The capsular bag 620 can retain the implant 500 within the eye 600 in a relationship relative to the eye 600 so that the optic body 630 refracts light directed to the retina (not shown). The leading haptic 635 and the trailing haptic 640 can engage the capsular bag 620 to secure the implant 500 therein. After delivering the implant 500 into the capsular bag 620, the nozzle 105 may be removed from the eye 600 through the incision 605, and the eye 600 can be allowed to heal over a period of time.

The systems, apparatuses, and methods described herein may provide significant advantages. For example, some embodiments may be particularly advantageous for delivering intraocular lenses. More particular advantages of some embodiments may include facilitating one-handed operation that can free up the second hand for other surgical instruments, which can in turn potentially reduce the number of staff required to a surgical procedure. Some embodiments may enhance delivery control and substantially reduce or eliminate stick-slip, which can allow for smoother delivery of an implant. Additionally, or alternatively, some embodiments may provide a single-handed reverse-drive mechanism, which can further enhance control of the delivery procedure.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations, the nozzle 105, the implant bay 110, and the actuator 115 may each be separated from one another or combined in various ways for manufacture or sale.

The claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for delivering an implant to an eye, the apparatus comprising:
    a gear rack configured to be coupled to the implant;
    a forward gearwheel;
    an input gearwheel meshed with the forward gearwheel;
    an actuation lever configured to rotate the input gearwheel;
    an idler gearwheel meshed with the input gearwheel;
    a reverse gearwheel meshed with the idler gearwheel; and
    a pivot arm operable to selectively engage the forward gearwheel and the reverse gearwheel to the gear rack.

2. The apparatus of claim 1, further comprising a ratchet wheel coupled to the actuation lever and the input gearwheel, the ratchet wheel configured to allow the actuation lever to rotate the input gearwheel in only one direction.

3. The apparatus of claim 1, further comprising an input shaft coupling the actuation lever to the input gearwheel.

4. The apparatus of claim 3, wherein the pivot arm is operable to pivot about the input shaft.

5. The apparatus of claim 3, wherein the pivot arm is mounted to the input shaft.

6. The apparatus of claim 1, wherein:
    the pivot arm is operable to rotate between a first position and a second position;
    the first position engages the forward gearwheel to the gear rack; and
    the second position engages the reverse gearwheel to the gear rack.

7. The apparatus of claim 6, further comprising a spring configured to return the pivot arm to the first position.

8. An apparatus for delivering an implant into an eye, the apparatus comprising:
    a gear rack configured to be coupled to the implant;
    a forward gearwheel meshed with the gear rack;
    an input gearwheel meshed with the forward gearwheel;
    a ratchet wheel coupled to the input gearwheel;
    an actuation lever configured to rotate the ratchet wheel in only one direction, thereby rotating the input gearwheel and the forward gearwheel to cause the gear rack to advance; and
    an input shaft coupling the actuation lever to the input gearwheel.

9. The apparatus of claim 8, further comprising:
    an idler gearwheel meshed with the input gearwheel;
    a reverse gearwheel meshed with the idler gearwheel; and
    a pivot arm operable to selectively engage the forward gearwheel and the reverse gearwheel to the gear rack.

10. The apparatus of claim 9 wherein the pivot arm is operable to pivot about the input shaft.

11. The apparatus of claim 9 wherein the pivot arm is mounted to the input shaft.

12. The apparatus of claim 9, wherein:
    the pivot arm is operable to rotate between a first position and a second position; the first position engages the forward gearwheel to the gear rack; and
    the second position engages the reverse gearwheel to the gear rack.

13. The apparatus of claim 12, further comprising a spring configured to return the pivot arm to the first position.

14. The apparatus of claim 8, further comprising:
    a nozzle having a delivery lumen;
    an implant bay coupled to the nozzle; and
    a push rod configured to couple the gear rack to the implant in the implant bay and advance the implant into the delivery lumen.

* * * * *